US00PP33660P2

(12) United States Plant Patent
Bierhuizen

(10) Patent No.: US PP33,660 P2
(45) Date of Patent: Nov. 23, 2021

(54) ***EUCALYPTUS* PLANT NAMED 'EUMIN106'**

(50) Latin Name: *Eucalyptus gunnii*
Varietal Denomination: Eumin106

(71) Applicant: Valérie Pouillart, Gien (FR)

(72) Inventor: Rodney Bierhuizen, Vineland (CA)

(73) Assignee: Valérie Pouillart, Gien (FR)

( * ) Notice: Subject to any disclaimer, the term of this patent is extended or adjusted under 35 U.S.C. 154(b) by 0 days.

(21) Appl. No.: 17/002,574

(22) Filed: Aug. 25, 2020

(51) Int. Cl.
*A01H 5/12* (2018.01)
*A01H 6/00* (2018.01)

(52) U.S. Cl.
USPC ..... Plt./216
CPC ..... *A01H 6/00* (2018.05)

(58) Field of Classification Search
USPC ..... Plt./216
CPC ..... A01H 6/00
See application file for complete search history.

*Primary Examiner* — Anne Marie Grunberg
(74) *Attorney, Agent, or Firm* — Penny J. Aguirre

(57) ABSTRACT

A new cultivar of *Eucalyptus gunnii* tree named 'Eumin106' that is characterized by its good winter hardiness for the species, its foliage that is silver-grey in color, and its compact plant habit.

2 Drawing Sheets

Botanical classification: *Eucalyptus gunnii.*
Varietal denomination: 'Eumin106'.

BACKGROUND OF THE INVENTION

The present invention relates to a new and distinct cultivar of *Eucalyptus gunnii* and will be referred to hereafter by its cultivar name, 'Eumin106'. 'Eumin106' represents a new cultivar of cider gum tree grown for landscape and container use.

'Eumin106' was discovered by the Inventor as a chance seedling in his garden in Ontario, Canada in 2005. The parentage is unknown.

Asexual propagation of the new cultivar was first accomplished by stem cuttings by the Inventor in 2005 in Ontario, Canada. Asexual propagation by stem cuttings has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Eumin106' as a new and unique cultivar of *Eucalyptus.*

1. 'Eumin106' exhibits good winter hardiness for the species.
2. 'Eumin106' exhibits foliage that is silver-grey in color.
3. 'Eumin106' exhibits a compact plant habit.

'Eumin106' can also be compared to typical plants of the species *Eucalyptus gunnii* and *Eucalyptus gunnii* cultivar 'Silverana' (not patented). Typical plants of *Eucalyptus gunnii* differs from 'Eumin106' in being less winter hardy, leaves that are more green in color and in having a less compact plant habit. 'Silverana' is similar to 'Eumin106' in cold hardiness. 'Silverana' differs from 'Eumin106' in having leaves that are less round in shape (more oboval) and more silver in color.

BRIEF DESCRIPTION OF THE DRAWINGS

The accompanying colored photographs illustrate the overall appearance and distinct characteristics of the new

*Eucalyptus*. The photographs were taken of an 18-month-old plant as grown in an unheated greenhouse in a 15-cm container in Gien, France.

Figure 1:
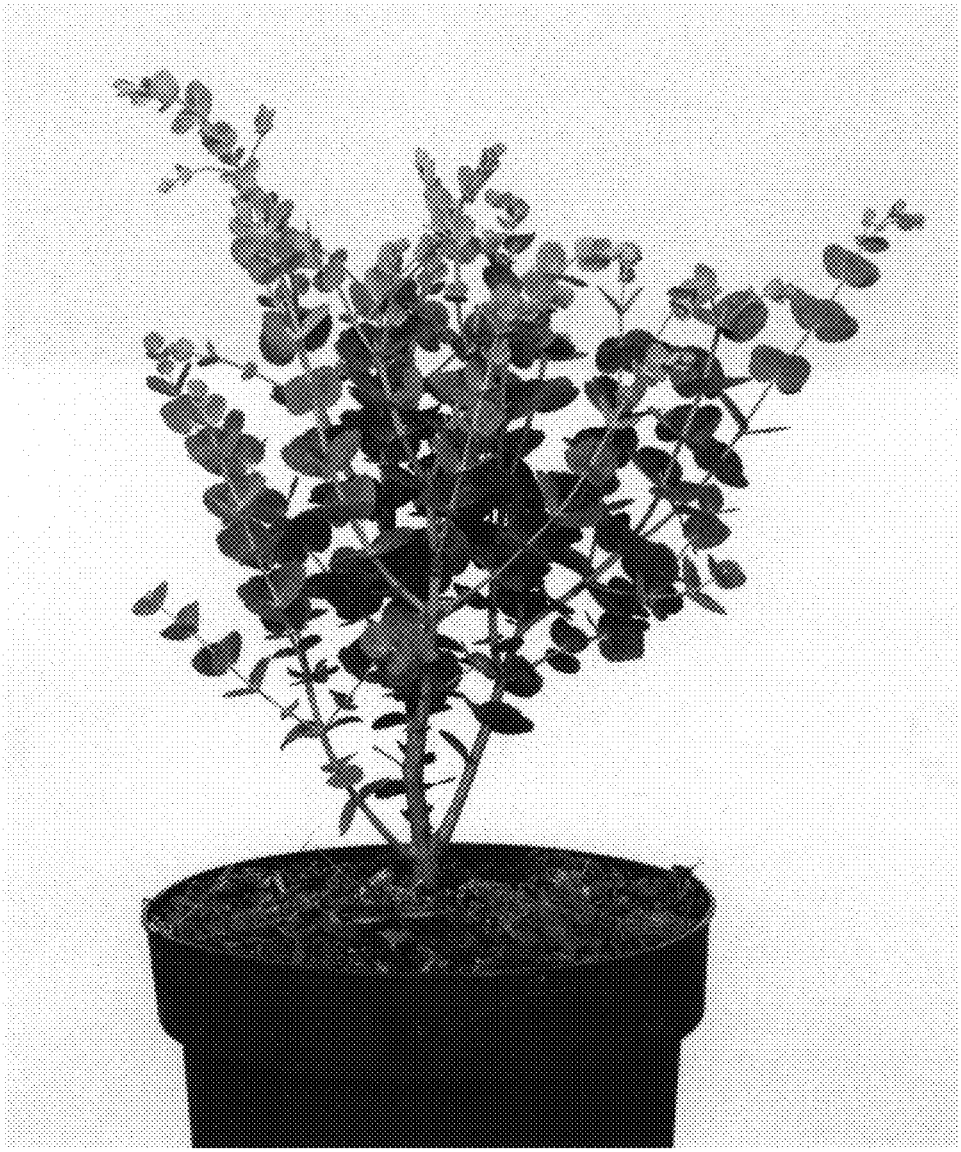

The photograph in FIG. 1 provides a side view of the plant habit of 'Eumin106'.

Figure 2:
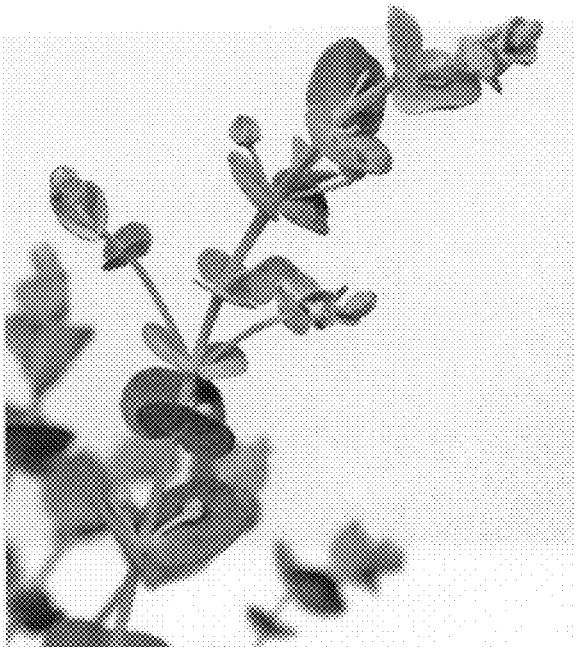

The photograph in FIG. 2 provides a close-up view of a young shoot of 'Eumin106'.

Figure 3:
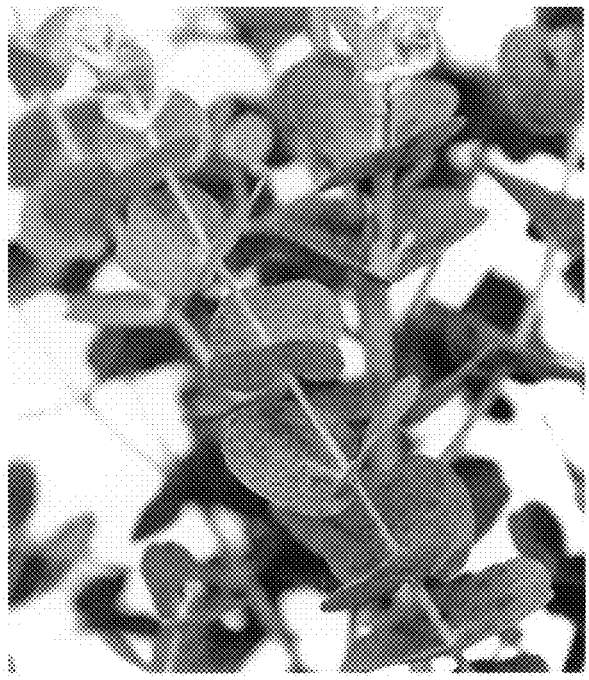

The photograph in FIG. 3 provides a close-up view of the mature foliage of 'Eumin106'.

The colors in the photographs are as close as possible with the photographic and printing technology utilized and the color values cited in the detailed botanical description accurately describe the colors of the new *Eucalyptus.*

DETAILED BOTANICAL DESCRIPTION OF THE PLANT

The following is a detailed description of 18-month-old plants of the new cultivar as grown in a conventional cold greenhouse in 15-cm containers in Gien, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen tree.

*Plant habit*.—Broadly upright, compact.

*Height and spread*.—An average of 25.5 cm in height and 21.4 cm in width as an 18-month-old plant in a 15-cm container.

*Cold hardiness*.—At least to U.S.D.A. Zones 6 to 7.

*Diseases and pests*.—No susceptibility or resistance to diseases or pests has been observed.

*Root description*.—Fibrous.

*Root development*.—Average of 15 days to initiate roots and a young rooted plant in a plug is produced in an average of 3 months in spring and summer and up to 5 months in the winter.

*Propagation type*.—Stem cuttings.

*Growth rate*.—Moderately vigorous.

Branch description:

*Branch shape*.—Rounded.

*Branch color*.—Young stems; a blend of 144B and 146C, sunny side strongly tinged with 183C, mature stems; 144A to 144B, older stems and bark of trunk; 199B, striped with N199A and N199B.

*Branch size*.—An average of 15.1 cm in length and 1.75 mm in diameter.

*Branch surface texture*.—Mature branches and trunk are slightly glossy and glabrous, young stems are matte due to waxy layer 188A in color, rhytidome presence was not observed on the plants available for data (too young).

*Branch aspect*.—Held in an average angle of 30°.

*Branch strength*.—Flexible and moderately strong.

*Internode length*.—An average of 1.7 cm.

*Branch quantity*.—An average of 3 main branches and 14 lateral branches per main branch.

*Branching habit*.—Main stems grow from the base and near the base with lateral branches, moderate branching.

*Insertion of primary branches onto main stem*.—Circular.

Foliage description:

*Leaf shape*.—Reniform.

*Leaf division*.—Simple.

*Leaf base*.—Hastate.

*Leaf apex*.—Broadly emarginate.

*Leaf venation*.—Pinnate, upper surface color 189A, lower surface a color between 146A and 147B.

*Leaf margins*.—Irregularly crenate.

*Leaf attachment*.—Sessile, amplexicaul.

*Leaf arrangement*.—Sub-opposite and opposite.

*Leaf surface*.—Both surfaces matte, upper surface; glabrous and covered with a thin waxy layer N189C in color, lower surface; glabrous and covered with a thin waxy layer a color between 189A and 189B.

*Leaf aspect*.—Flat, held in an average angle of 65° to lateral branch (varying between 50° and 80°).

*Broadest portion of leaf blade*.—Middle.

*Leaf color*.—Young upper surface; a color between NN137C and 189A, covered with a thin waxy layer N189C, young lower surface; a color between NN137D to 138B, covered with a thin waxy layer 189A to 189B, mature upper surface; 189A, but slightly darker, covered with a thin waxy layer N189C, mature lower surface; NN137D, covered with a thin waxy layer 189A to 189B.

*Leaf number*.—Average of 18 per lateral branch (9 pairs).

*Leaf size*.—An average of 1.8 cm in length, 2.1 cm in width.

Flower description: No flowers have been produced to date, assumed to be non-flowering.

It is claimed:

1. A new and distinct cultivar of *Eucalyptus* tree named 'Eumin106' as herein illustrated and described.

* * * * *